United States Patent [19]

Poe et al.

[11] 4,126,750

[45] Nov. 21, 1978

[54] PROCESS FOR THE HIGH PRESSURE METHYLATION OF 2,6-XYLENOL

[75] Inventors: Ronald L. Poe, Ponca City, Okla.; John F. Scamehorn, Austin, Tex.; Cortlan R. Schupbach, Ponca City, Okla.

[73] Assignee: Continental Oil Company, Ponca City, Okla.

[21] Appl. No.: 857,052

[22] Filed: Dec. 5, 1977

Related U.S. Application Data

[62] Division of Ser. No. 788,198, Apr. 18, 1977.

[51] Int. Cl.² .............................................. C07C 37/12
[52] U.S. Cl. ..................................................... 568/804
[58] Field of Search ....................... 260/621 R, 624 L

[56] References Cited

U.S. PATENT DOCUMENTS

| | | | |
|---|---|---|---|
| 3,867,466 | 2/1975 | Endou et al. | 260/621 R |
| 3,979,464 | 9/1976 | Leach | 260/621 R |

Primary Examiner—James O. Thomas, Jr.
Assistant Examiner—Werren B. Lone
Attorney, Agent, or Firm—Cortlan R. Schupbach, Jr.

[57] ABSTRACT

High pressure methylation of 2,6-xylenol to produce 2,3,6-trimethylphenol is accomplished by maintaining the methanol/2,6-xylenol feed at temperature and pressures sufficient to keep the feed liquid in a reactor head then forcing the feed through orifices, expanding the feed into a mixed vapor liquid phase, the feed after expansion being in the range of reaction conditions of pressure and temperature while in the presence of the catalyst where the reaction takes place. The process avoids the current problems of uneven feed mixtures and catalyst tube plugging.

3 Claims, 3 Drawing Figures

PROCESS FOR THE HIGH PRESSURE METHYLATION OF 2,6-XYLENOL

This case is a divisional of Ser. No. 788,198 filed Apr. 18, 1977.

This invention relates to a process for the high pressure methylation of 2,6-xylenol to form 2,3,6-trimethylphenol. More particularly this invention relates to the high pressure methylation of 2,6-xylenol by heating the methanol/xylenol feed, maintaining the heated feed under pressure and expanding through orifices into the presence of the catalyst such that an even mixture of xylenol and methanol is present during reaction.

An efficient method for producing 2,3,6-trimethylphenol from 2,6-xylenol by the high pressure liquid phase methylation of 2,6-xylenol over an alumina catalyst using methanol as a methylating agent has been described in U.S. Pat. No. 3,979,464. The process taught is carried out commercially using a bundle of small diameter reaction tubes with a heat transfer fluid flowing on the outside of the tubes to carry away the heat of the reaction so the temperature remains within the optimum range throughout the reactor for the period of reaction. In practice the feed normally travels through a preheater before entering the reactor to raise the feed temperature to reaction levels. The reaction temperature is critical since when the temperature is too low the reaction occurs at a negligible rate and when the temperature is too high, the catalyst rapidly deactivates. However, in commercial reactors a major problem with the liquid feed system has developed in that the feed, upon leaving the necessary preheater at reaction temperatures, may be partially vaporized. The vapor in the feed contains a major proportion of methanol and a minor proportion of 2,6-xylenol. This partially vaporized feed is then fed to a reactor head which is essentially an open chamber available to all catalyst containing reactor tubes. As the vapor and liquid enter the head, even distribution of liquid and gas in the multiple tubes of the reactor is not found. The optimum ratios of methanol to 2,6-xylenol is not found in every tube, leading to poor conversion, poor selectivity to desired product, and carbon plugging of some reactor tubes due to coking on the catalyst.

That this problem has long been known in multiple reactors is shown by U.S. Pat. No. 3,929,421, which teaches a tubular catalytic reactor having premixing means for multiple reactants having different densities. However this patent deals with mixtures of immiscible fluids and provides a reactor which is complicated, has many operating parts, and which normally operates with an upward flow. Such a reactor is not efficient for mixtures of fluid and vapor and requires a particulate bed at one end to equalize the mixing of the two immiscible fluids. Clearly such a reactor is nonadaptable to other systems and is especially not feasible for the system of the high pressure methylation of 2,6-xylenol.

It would therefore be of great benefit to provide a method for the high pressure methylation of 2,6-xylenol to produce 2,3,6-trimethylphenol, which is a valuable intermediate in the preparation of vitamin E.

It is therefore an object of the instant invention to provide a method for equalizing feed compositions in all tubes of a horizontal or vertical multiple tube reactor while maintaining high reactivity and selectivity to the desired product. Other objects will become apparent to those skilled in this art as the description proceeds.

It has now been discovered in accordance with the instant invention that 2,6-xylenol can be methylated in the liquid phase under high pressure using methanol over alumina catalysts by maintaining the feed from the preheater under pressures sufficient to maintain the feed mixture in the liquid state until the reactor head is entered, then expanding and cooling the feed by injection through orifices into each reactor tube partially filled with catalysts. The feed after expansion is at a temperature and pressure sufficient and preferably optimum, for the reaction to occur. After flashing across the orifice, the feed will contact the catalyst as a vapor/liquid mixture, or as a liquid under some conditions. After the reaction, a mixture of vapor and liquid is present. In vertical reactors, this vapor rises and attempts to reenter the entrance chamber to the reactor tubes where vapor upsets the balance of 2,6-xylenol/methanol. The present invention of injecting the feed through orifices into the reactor tubes avoids all these problems. This method is simple and provides a highly reliable system with a minimum of working parts not found in current reactor systems.

Briefly describing the attached drawings, FIG. 1 is a vertical sectional view of the present invention showing the operative feature in relation to the reactor tubes having catalysts therein.

The following detailed description will show the difficulties of achieving a substantially equal distribution of a liquid gas mixture over a predetermined zone which opens directly onto a plurality of tubes in a tubular reactor, as well as a method for achieving an even mixture of feed throughout the reactor.

Figure 1:
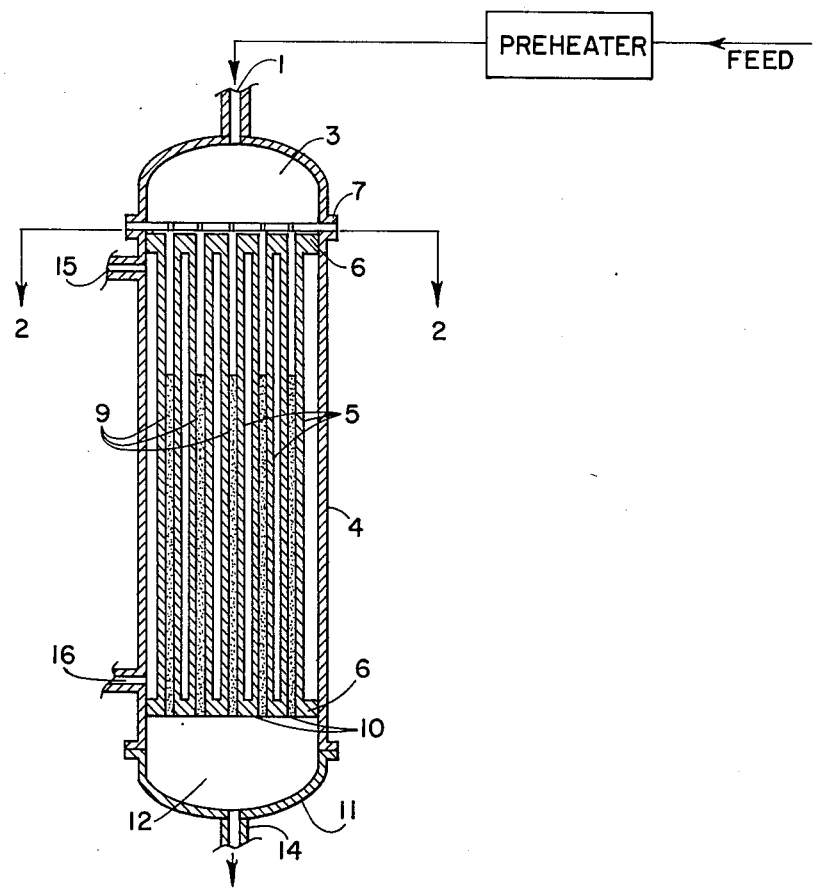

In FIG. 1 the methanol/xylenol feed under sufficient pressure to maintain said feed in a liquid state as the feed exits the preheater enters the apparatus through the fluid inlet 1 which is mounted on a first housing means 2. The first housing means is in fluid and vapor tight conjunction with an enclosing means 4 surrounding a plurality of reactor tubes 5 in a substantially laterally spaced orientation to each other, each tube penetrating a mounting plate 6 at each opposed end of each tube, said tube being connected to said mounting plates and sealed at each opposed end of the tube, said seal being vapor and fluid tight. Each tube contains a particulate alumina-based catalyst. Said first housing means 2 is joined to the enclosing means 4 in a fluid and vapor tight conjunction to provide an entrance chamber common to all tubes, said entrance chamber being a fluid and vapor tight chamber. Interposed between the housing means and the enclosing means is a plate having at least one orifice opening into each reactor tube, said plate being in vapor and fluid tight conjunction with the joint between the first housing means and the enclosing means respectively. Each tube 5 is at least partially filled with a catalyst 9 which is held in the tubes by a restraining means 10, said restraining means being disposed such that fluids and vapors may pass therethrough. On the opposite ends of said enclosing means 4 from said housing means 2 is joined in a fluid and vapor tight conjunction with said enclosing means a second housing means 11 providing an exit chamber 12 from said tubes. The reaction products of the reaction then exit the reactor through an exit orifice 14. A heat exchange fluid is circulatable around the outside walls of tubes 5 in a shell 4 equipped with entrance and exit ports (15 and 16).

The tubes 5 are filled with a fixed bed particulate catalyst. When a catalyst is used, a screen or the like 10 may be transversely extended across the plate 6 through which tubes 5 are mounted to hold the bed particulate matter 9 in place. When the reaction carried out is the methylation of 2,6-xylenol to produce 2,3,6-trimethylphenol, the catalyst is an alumina catalyst.

Figure 2:
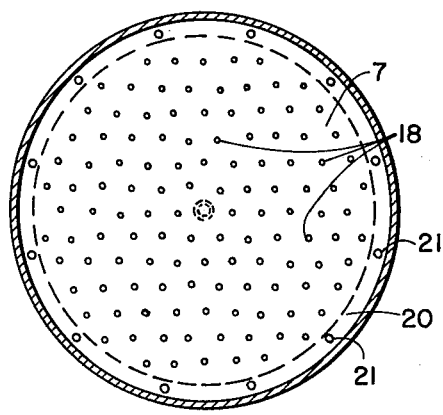
FIG. 2 is a transverse sectional view taken along the line A,A of FIG. 1.
Figure 3:
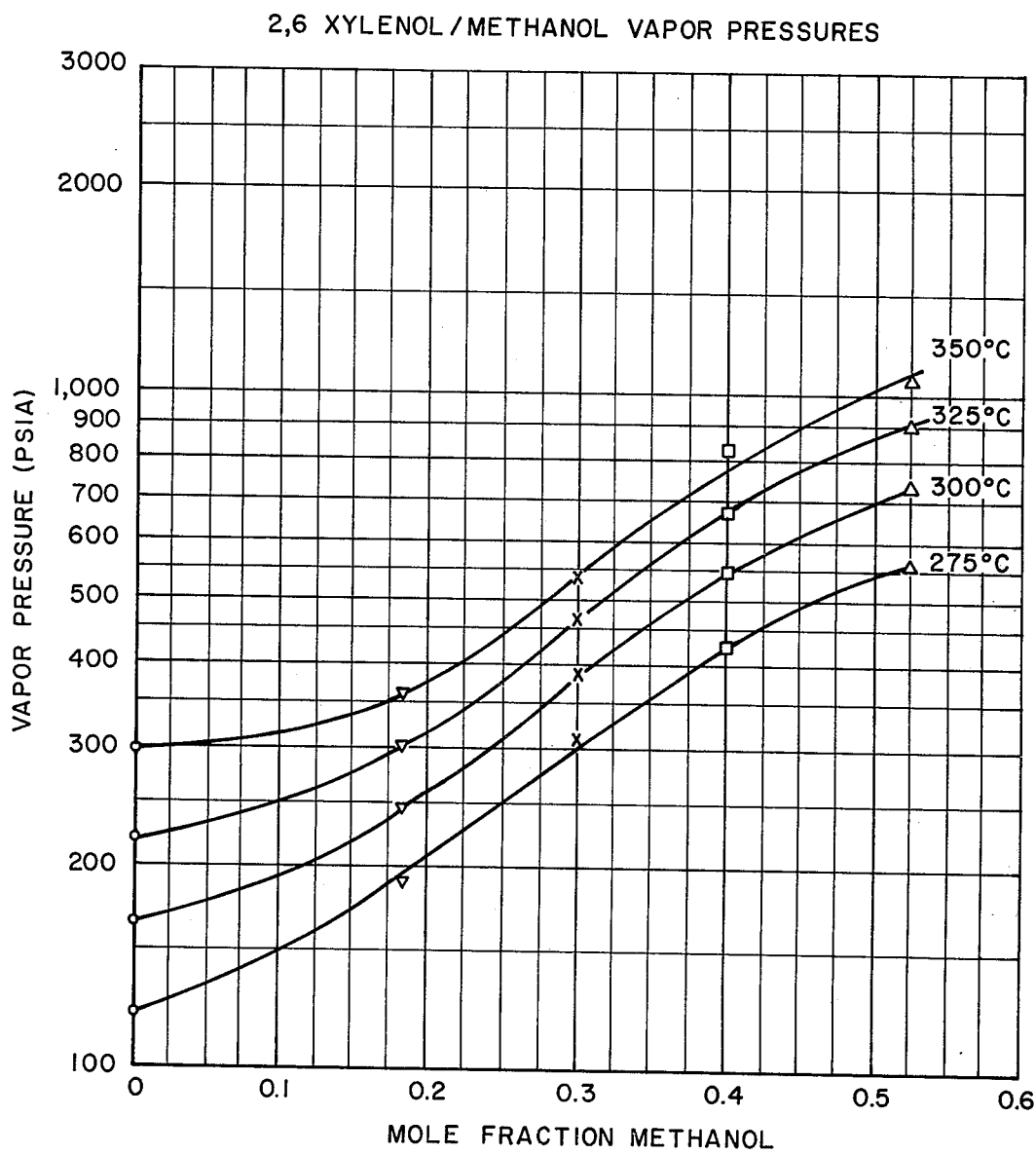
FIG. 3 is a graph which relates vapor pressure in pounds per square inch actual with the mole fraction of methanol in the feed at temperatures of from 275° C to 350° C in 25° increments. The figure illustrates vapor pressures of 2,6-xylenol/methanol mixtures.

Plate 7 containing the orifices through which the liquefied feed material passes into the reaction tubes is shown in greater detail in FIG. 2. As the liquid feed contacts plate 7 the liquid passes through the apertures 18 therein, said plate defining a temperature and pressure drop from the upstream side to the downstream side respectively. This temperature drop allows a portion of the liquefied feed to vaporize into a liquid gaseous mixture in the reactor tubes at the desired reaction conditions as the reaction continues to completion. An outwardly projecting flange or ring 20 is provided to hold orifice 7 in place, said flange containing apertures for a plurality of nut and bolt assemblies 21 extending through aligned holes in the respective orifice plate 7, first housing means 2 and the enclosing means 4 in order to provide a fluid and vapor tight conjunction.

Plate 7 containing orifices 18 will contain at least one orifice for each of the reactor tubes 5. It can be clearly seen that the orifice size is interdependent with the temperature and pressure of the feed in the reactor head 3. The orifice size may be varied to fit the desired conditions; however, the smaller the orifice size the more precise the control which can be exerted over the temperature and pressure conditions of the liquid feed. The orifice size will be in practice sufficient to allow expansion from a liquified feed to a vapor/liquid mixture in the reactor tubes at the reaction conditions desired. Since the feed to the reaction must be maintained in the liquid state until passage through the orifice is complete, orifice size is calculated based upon the drop in temperature and pressure from the entrance chamber 3 to the reactor tubes 4. It is desired that the temperature in the reactor tubes be from about 300° to 390° C and the pressure be from about 350 to about 1500 pounds per square inch gauge. Preferred reaction conditions are from 340° C to 375° C and from about 400 to about 550 pounds per square inch gauge. Normally the mole ratio of methanol to 2,6-xylenol in the reaction feed will be from about 0.1 to about 1 respectively.

The instant invention thus defines an improved reactor apparatus comprising;
(a) a plurality of reactor tubes in a substantially laterally spaced orientation to each other, each tube penetrating a mounting plate at each opposed end of said tube, said tube being connected to said mounting plates and sealed at opposed ends of each tube, said seal being vapor and fluid tight, each tube containing a particulate catalyst,
(b) an enclosing means surrounding said tubes in a fluid and vapor tight conjunction and providing inlet and outlet means for circulation of a heat exchange fluid therethrough,
(c) a first housing means at one end of said reactor tubes connected to said enclosing means and providing an entrance chamber common to said tubes, said entrance chamber being a fluid and vapor tight chamber and,
(d) a second housing means at the opposite ends of said reactor tubes connected to said enclosing means and providing an exit chamber from said tubes, said exit chamber being a fluid and vapor tight chamber common to all reaction tubes, the improvement comprising a plate inserted between said first housing means and said enclosing means in a fluid and vapor tight conjunction, said plate containing at least one orifice opening into each reactor tube, said orifice being of a size sufficient to cause sufficient pressure drop on the downstream side of the orifice to partially vaporize said feed mixture to reach reaction conditions before contacting said catalysts at specific conditions of pressure and temperature.

Likewise, the invention provides an improved method and apparatus for producing 2,3,6-trimethylphenol from 2,6-xylenol by contacting said xylenol with methanol in the presence of alumina catalysts at temperatures of from about 300° to about 390° C and pressures of from about 350 to about 1500 pounds per square inch gauge in a tubular reactor, the improvement comprising optimizing the mole ratio of reactants by;
(a) preheating the liquid 2,6-xylenol/methanol feed mixture in substantial absence of alumina,
(b) injecting and expanding said feed mixture into reactor tubes containing sufficient alumina to catalyze said reaction, said injection into each tube being made through at one orifice of sufficient size to cause sufficient pressure drop on the downstream side of the orifice to partially vaporize said feed mixture to desired reaction conditions before contacting said catalyst,
(c) said preheating being carried out to a temperature sufficient to maintain reaction temperatures and pressures after expansion.

It is thus clear that the instant invention proposes a reactor configuration which solves the previous problems of uneven feed in the reactor tubes with consequent plugging and nonselectivity and reaction rates. The invention is more concretely described with reference to the example below wherein all parts and percentages are by weight unless otherwise specified. The example is intended to illustrate the instant invention and not to limit it. The example presented gives the vapor pressure of mixtures of 2,6-xylenol about 99 weight percent pure and methanol at several temperatures and methanol contents. A 10–15 weight percent (about 30–40 mole percent) methanol composition is typical of the feeds normally used in these systems.

If the pressure of the feed is above the vapor pressure of the mixture, the stream will completely liquify. The present invention provides that the presence at the entrance to the reactor tubes be maintained above the vapor pressure of the feed mixture at reaction temperatures, optimum reaction temperatures being described above. The feed in the entrance chamber 3 will be liquefied under normal reaction pressures and temperatures and feed compositions.

Since these reaction conditions are near the critical region, it should be noted that the feed temperature could be maintained above the critical temperature of the mixture (the highest temperature in the system at which the vapor and liquid can co-exist) and the feed can be maintained as one phase by the use of temperature. However, it has been shown that at these temperatures decomposition of the feed is rapid and runaway reactions can insue in the first portion of the reactor under some conditions unless special measures such as catalyst dilution are instituted. Mixture critical temperatures are shown in Table 1 for 2,6-xylenol/methanol mixtures. The actual temperature of interest in the instant inventions is the cricondentherm which is only slightly greater than the critical temperature and thus desired conditions are adequately obtained in the instant process. The critical factor in the instant process is keeping the feed pressurized and preventing vapor from entering the reactor head, while allowing a vapor/liquid mixture in the reactor tubes. Generally, a smaller orifice size allows a greater range of temperature and pressure variations than possible with larger orifices.

EXAMPLE 1

A feed material composed of 37.5 mole percent methanol and 62.5 mole percent 2,6-xylenol is preheated and sent to the reactor at a liquid hourly space velocity of 4.0. The reactor is maintained at a pressure of 450 psig and 355° C. The orifice size in the reactor tube inlets and the preheater temperature are determined such that (1) the pressure in the head is greater than the mixture vapor pressure and (2) the feed material is at reactor conditions after flashing across the orifice. The conversion of 2,6-xylenol is about 32.1% and the selectivity towards 2,3,6-trimethylphenol is about 50.5%.

Critical temperatures for various feed compositions are shown in Table 1 below ranging from 100% 2,6-xylenol to 100% methanol.

Table 1

| Feed Composition | Critical Temperature (° C) |
|---|---|
| 100% Methanol | 239 |
| 80 w/o Methanol, 20 w/o 2,6-xylenol | 264 |
| 60 w/o Methanol, 40 w/o 2,6-xylenol | 296 |
| 40.9 w/o Methanol, 59.1 w/o 2,6-xylenol | 379 |
| 28.2 w/o Methanol, 71.8 w/o 2,6-xylenol | 406 |
| 14.9 w/o Methanol, 85.1 w/o 2,6-xylenol | 417 |
| 100% 2,6-xylenol | 428 |

The conversion levels obtained in the practice of the example will be substantially the same as those shown in the previously referenced U.S. Pat. No. 3,979,464. The process of the instant invention operates at substantially the same reaction conditions of temperature, feed ratios, pressures and weight hourly space velocities. Consequently, the vapor/liquid distribution to each tube reactor is sufficiently uniform with respect to distribution and flow characteristics to produce optimal conversion results in an alumina catalyst bed.

Finally, the mixture in the tubular reaction zones is subjected to predetermined liquid phase conditions of temperature, catalyst and time, the resulting reaction mixture exiting from the ends of the tubular zones and collected in the common exit chamber. The reaction mixture or product is then removed from the exit chamber through the exit port 14.

While certain embodiments and details have been shown for the purpose of illustrating this invention, it will be apparent to those skilled in this art that various changes and modifications may be made herein without departing from the spirit or the scope of the invention.

We claim:

1. In a method for producing 2,3,6-trimethylphenol from 2,6-xylenol by contacting said xylenol with methanol in the presence of alumina catalysts at temperatures of from about 300° to about 390° C and pressures of from about 350 to about 1500 pounds per square inch gauge in a reactor having a plurality of reactor tubes the improvement comprising optimizing the mole ratio of reactants in each reactor tube by
   (a) preheating the liquid 2,6-xylenol/methanol feed mixture in substantial absence of alumina while maintaining sufficient pressure to maintain the feed mixture in the liquid state,
   (b) injecting and expanding said feed mixture into reactor tubes containing sufficient alumina to catalyze said reaction, said injection into each tube being made through at least one orifice of sufficient size to cause sufficient pressure drop on the downstream side of the orifice to partially vaporize said feed mixture to reach reaction conditions before contacting said catalyst,
   (c) said preheating being carried out to a temperature sufficient to maintain reaction temperatures and pressures after expansion.

2. A method as described in claim 1 wherein the reaction takes place at temperatures of from about 340° to about 375° C and pressures of from about 400 to about 550 pounds per square inch actual.

3. A method as described in claim 2 wherein the mole ratio of reactants is from about 0.1 to about 1.0 respectively.

* * * * *